United States Patent
Stiver et al.

(10) Patent No.: US 10,967,341 B2
(45) Date of Patent: Apr. 6, 2021

(54) MIXING DEVICE

(71) Applicant: TECAN TRADING AG, Mannedorf (CH)

(72) Inventors: Larry Stiver, Cary, NC (US); Vincent Ahlheit, Apex, NC (US); Peter Siesel, Briarcliff Manor, NY (US); Dominic Erb, Winterthur (CH); Klaus Lun, Pfaffikon SZ (CH); Christoph Karthaus, Jona (CH)

(73) Assignee: TECAN TRADING AG, Mannedorf (CH)

( * ) Notice: Subject to any disclaimer, the term of this patent is extended or adjusted under 35 U.S.C. 154(b) by 369 days.

(21) Appl. No.: 16/044,661

(22) Filed: Jul. 25, 2018

(65) Prior Publication Data

US 2020/0030759 A1 Jan. 30, 2020

(51) Int. Cl.
*B01F 11/00* (2006.01)
*B01F 3/12* (2006.01)
*B01F 15/02* (2006.01)
*C12M 3/06* (2006.01)

(52) U.S. Cl.
CPC ........ *B01F 11/0017* (2013.01); *B01F 3/1221* (2013.01); *B01F 15/0202* (2013.01); *B01F 11/0008* (2013.01); *B01F 15/0222* (2013.01); *B01F 2003/1285* (2013.01); *C12M 27/16* (2013.01)

(58) Field of Classification Search
CPC .............. B01F 11/0008; B01F 11/0017; B01F 3/1221; B01F 15/0202; B01F 2003/1285; B01F 15/0222; C12M 27/16
See application file for complete search history.

(56) References Cited

U.S. PATENT DOCUMENTS

| | | | | |
|---|---|---|---|---|
| 3,109,084 A | * | 10/1963 | Walsh | B01L 7/00 219/385 |
| 3,674,198 A | * | 7/1972 | Eberle | B04B 5/0414 494/7 |
| 4,202,634 A | * | 5/1980 | Kraft | B01F 11/0031 366/111 |
| 4,284,603 A | * | 8/1981 | Korom | B01L 9/06 210/323.1 |
| 4,747,693 A | * | 5/1988 | Kahl | B01F 11/0008 211/74 |
| 4,938,369 A | * | 7/1990 | Carilli | B01L 9/06 211/60.1 |
| 5,215,376 A | * | 6/1993 | Schulte | B01F 11/0002 141/265 |
| 5,632,388 A | * | 5/1997 | Morrison | B01L 9/06 211/170 |

(Continued)

FOREIGN PATENT DOCUMENTS

EP 3599013 A1 * 1/2020 .......... B01F 11/0017

*Primary Examiner* — Tony G Soohoo
(74) *Attorney, Agent, or Firm* — Notaro, Michalos & Zaccaria P.C.

(57) ABSTRACT

A mixing apparatus, comprising a drive unit (1) with a drive (10) and a shaft (11) which is pivotable about a pivot axis (A) and which is operatively connected to the drive (10), a pivot receptacle (2) which is arranged on the shaft (11), wherein the pivot axis (A) is substantially horizontally aligned, wherein the pivot receptacle (2) comprises a base (20) on which receptacles (21, 22) are provided which extend away from the base (20) and into which holders (3) for containers (7) are insertable.

17 Claims, 8 Drawing Sheets

(56) References Cited

U.S. PATENT DOCUMENTS

| | | | | |
|---|---|---|---|---|
| 5,918,979 A * | 7/1999 | Martin | ............... | B01F 11/0005 366/211 |
| 5,996,818 A * | 12/1999 | Boje | ............... | B01L 9/06 206/443 |
| 6,059,446 A * | 5/2000 | Dschida | ............... | B01F 11/0008 366/208 |
| 6,132,684 A * | 10/2000 | Marino | ............... | B01L 9/06 211/74 |
| 6,640,981 B2 * | 11/2003 | Lafond | ............... | B01L 9/06 206/443 |
| 6,920,986 B2 * | 7/2005 | Lacombe | ............... | B25H 3/003 211/70.6 |
| 7,220,590 B2 * | 5/2007 | Moritz | ............... | B01L 9/543 422/561 |
| 7,282,182 B2 * | 10/2007 | Dale | ............... | B01L 9/06 422/562 |
| 8,017,094 B2 * | 9/2011 | Meyer | ............... | G01N 35/04 422/560 |
| 8,501,115 B2 * | 8/2013 | Adey | ............... | B01F 11/0008 422/500 |
| 8,550,696 B2 * | 10/2013 | Ebers | ............... | B01F 11/0008 366/209 |
| 8,915,154 B2 * | 12/2014 | Ross | ............... | G01N 1/286 73/864.91 |
| 9,144,801 B2 * | 9/2015 | Johnson | ............... | B01L 9/06 |
| 9,457,350 B2 * | 10/2016 | Dickinson | ............... | B01L 7/02 |
| 9,776,188 B1 * | 10/2017 | Kamees | ............... | B01L 9/06 |
| 9,802,200 B2 * | 10/2017 | Taylor | ............... | B01L 9/06 |
| 10,376,052 B1 * | 8/2019 | Bartley | ............... | A47B 81/005 |
| 2001/0002985 A1 * | 6/2001 | Kleinsasser | ............... | B01F 11/0017 422/562 |
| 2015/0217291 A1 * | 8/2015 | Wilson | ............... | G01N 35/04 435/286.1 |
| 2020/0030759 A1 * | 1/2020 | Stiver | ............... | B01F 11/0017 |

* cited by examiner

MIXING DEVICE

BACKGROUND OF THE INVENTION

This invention concerns a mixing apparatus, especially for mixing substances in closed containers.

DESCRIPTION OF THE PRIOR ART

Mixing apparatuses are known from the prior art, in which, for example, perforable ampoules can be arranged on a tilting table, which can be pivoted by means of a drive. The tilting table comprises individual specific holders for ampoules of different diameters or the tilting table comprises a pattern of fingers which protrude from the table top and between which different ampoules can be arranged, wherein smaller ampoules roll back and forth between the fingers during tilting.

In another known mixing apparatus, a holder for ampoules is rotatably mounted on two sides, wherein the holder can be pivoted by means of a drive. An ampoule can be inserted in each container receptacle of the holder.

With such mixing apparatuses, there is a risk that the ampoules may be confused before or during insertion into the holder or that the ampoules may be confused when removed from the holder. In addition, the insertion and removal of the ampoules is time-consuming.

DESCRIPTION OF THE INVENTION

One of the objects of the present invention is to provide a mixing apparatus in which the risk of confusion is reduced and in which the insertion and removal of containers containing substances to be mixed is facilitated.

This object is achieved by the mixing apparatus with the characteristics of claim 1. Other embodiments of the mixing apparatus, a mixing plant and a method for operating a mixing apparatus or a mixing plant are defined by the features of further claims.

A mixing apparatus according to the invention comprises a drive unit with a drive and a shaft which is pivotable about a pivot axis and which is operatively connected to the drive, a pivot receptacle which is arranged on the shaft, wherein the pivot axis is essentially horizontally aligned, wherein the pivot receptacle comprises a base on which receptacles are provided which extend away from the base and into which holders for containers can be inserted. With such a design it is possible to insert the containers independently of the mixing apparatus, i.e. before introducing them in the mixing apparatus into the holder. The insertion can therefore take place in a short time. Moreover, the containers cannot be confused during insertion, as they can be arranged in a holder beforehand without time pressure.

The drive unit comprises a housing in which an electromechanical drive, with or without gear unit, is arranged. The base can be designed as a plate or as a frame.

In an embodiment, the pivot receptacle can be pivoted by any angle in both directions about the pivot axis. This means, for example, that the pivot receptacle can be pivoted back and forth by means of the drive unit by any angle or that the pivot receptacle can be rotated once or several times about the pivot axis in one of the two directions of rotation. This allows an optimal mixing of all possible substances which may be present in the containers. Powders or fluids such as suspensions or emulsions can therefore be mixed. For example, whole blood, i.e. blood plasma or blood serum with blood cells, can be mixed for itself or with additional substances. For example, the substances to be mixed can be filled into reagent tubes or perforable ampoules. Perforable ampoules contain glass or plastic containers, which are closed at the top with a lid which contains a septum. The septum comprises a soft plastic, for example made of PTFE or silicone, which can be pierced with a pipette needle or tip. For example, such a cover can be screwed with a thread onto the container open at the top.

In an embodiment, the mixing apparatus comprises a control unit with which the pivot angle, pivot speed and pivot direction can be adjusted. By setting these values, an optimal mixture of substances can be achieved.

In an embodiment, the receptacles include first receptacles arranged in an area of the base near the shaft and second receptacles arranged in an area of the base remote from the shaft. The holders can be inserted with a first end into the first receptacle and with a second end into the second receptacle. Thus, the position and orientation of each holder is clearly and reliably determined. Between one of the first receptacles and second receptacles aligned therewith in the direction of the pivot axis, further receptacles aligned with it may be provided. The additional receptacles give the holders additional support or they allow the insertion of shorter holders which do not extend over the entire length of the pivot receptacle.

In an embodiment, the receptacles comprise elevations which can protrude into complementary recesses in the ends of the holders. For example, the elevations are elements that extend directly from the base of the pivot receptacle. The elevations can be pins, for example pins with a circular cross-section. However, other cross-sections are also conceivable. The elevations can also be sliding blocks, for example for T-slots or dovetail grooves. Of course, the receptacles can also include recesses into which complementary elevations of the ends of the holders can protrude, and which also form a pin-bore connection or a groove stone-and-groove connection.

In an embodiment, several receptacles are arranged next to each other in a direction transversely to the pivot axis. This allows several identical or different holders to be inserted side by side into the pivot receptacle, allowing the contents of several containers to be mixed simultaneously. For example, the receptacles are arranged symmetrically with respect to the pivot axis.

In an embodiment, the mixing apparatus comprises first spacers which can be inserted into the receptacles and into which the holders for the containers can be inserted, and second spacers which are arranged between the receptacles and on which the holders for the containers can rest. With the spacers, the distance between the inserted holders and the base of the pivot receptacle increases. This is advantageous if shorter containers are to be inserted into the holders and the upper end of the inserted containers should have essentially the same distance from the base as the longer containers. By varying the thickness of the spacers, it is possible to achieve that the upper ends of the common containers are essentially aligned with each other when they are in the mixing apparatus. Different spacers can be arranged simultaneously on the pivot receptacle, allowing different containers to be arranged simultaneously in the mixing apparatus and whose upper ends are essentially in alignment with each other.

In an embodiment, the pivot receptacle is equipped with third receptacles on the side of the receptacles, with which a retaining element can be arranged fixed or removable at least in the area between the receptacles at a distance from the base.

In an embodiment, the third receptacles are designed in such a way that the retaining element can be detachably or slidably arranged therein. Accordingly, a detachable retaining element can be provided or a sliding element can be provided with which the retaining element can be moved or pivoted in a plane.

In an embodiment, the mixing apparatus comprises a bearing unit which is located opposite the drive unit with respect to the pivot receptacle and in which the pivot receptacle is mounted in alignment with the shaft. As the pivot receptacle is mounted on both sides, the corresponding bearings and the pivot receptacle can be dimensioned with less stability, which means that they take up less space and require less mass to be moved.

In an embodiment, the mixing apparatus comprises at least one holder for containers, which can be inserted into the receptacles.

In an embodiment, each holder comprises several container receptacles arranged along a longitudinal axis, which are formed between the two ends. The container receptacles can, for example, be countersunk bores with a circular cross-section. However, other cross-sections are also possible. Each container receptacle can have at least one lateral opening which extends laterally outwards from the respective container receptacle transversely to the longitudinal axis. The at least one opening can be a slot or a window. Each container receptacle can comprise two lateral openings, which are arranged opposite each other relative to the longitudinal axis and which together with the container receptacle form a passage in the holder. Each container receptacle can therefore be assigned a slot and a window, two slots or two windows.

Each window of the holder can be equipped with a clamping lug which projects through the window into the respective container receptacle, so that a container accommodated therein can be clamped therein. On the side of the holder that surrounds the windows, a tab plate can be arranged on the holder that surrounds all clamping lugs.

In an embodiment, the mixing apparatus comprises at least one retaining element, which is arranged in the third receptacles.

In an embodiment, the retaining element comprises a perforated plate, with the holes being arranged so that they are aligned with the container receptacles formed in the holder, wherein the internal dimensions of the holes are smaller than the internal dimensions of the container receptacles.

The mentioned embodiments of the mixing apparatus can be used in any combination, provided they do not contradict each other.

A mixing plant according to the invention comprises a machine stand on which a mixing apparatus according to the invention is arranged.

The mixing plant can comprise a working surface which is arranged on the machine stand and wherein the mixing apparatus is arranged on the working surface.

In an embodiment, the mixing plant comprises a pipetting unit with which fluids can be supplied to or removed from containers in the mixing apparatus.

In an embodiment, the pipetting unit comprises a transport unit on which pipette tips are arranged and with which the pipette tips can be moved horizontally and/or vertically in an area above the machine stand or above the working surface.

In an embodiment, the mixing plant comprises a reading unit with which labels can be read from the containers to be received by the mixing apparatus. The labels can be selected from the group that includes 1D barcode, 2D barcode, RFID tag and the like.

The mentioned embodiments of the mixing plant can be used in any combination, as long as they do not contradict each other.

A method according to the invention for operating a mixing apparatus or a mixing plant comprises the steps:
Provision of a mixing apparatus according to the invention;
Inserting a holder with containers arranged therein into the receptacles of the pivot receptacle; and
Pivoting the pivot receptacle around the pivot axis with the drive unit.

The introduction can be an insertion, for example if the pivot receptacle includes cylindrical pins and the holder is provided with correspondingly complementary bores. The introduction can also be pushing in, for example if the pivot receptacle includes sliding blocks and the holder is provided with a correspondingly complementary groove.

In an embodiment, the method comprises the steps:
Removing the retaining element before inserting the holder; and
Attaching the retaining element after inserting the holder.

For example, fastening elements can be removed which fix the retaining element in the corresponding receptacles and the retaining element can then be lifted off and placed at another location independently of the mixing apparatus. Alternatively, the retaining element can be moved linearly away from the area above the pivot receptacle by means of a sliding mechanism. In another alternative, the retaining element can be pivoted away from the area above the pivot receptacle in a plane by means of a rotation mechanism. If the retaining element is fixedly arranged on the pivot receptacle, the holder must be pushed into the pivot receptacle under the retaining element, for example along the pivot axis.

In an embodiment, the method comprises the step:
Reading in labels of the containers arranged in a holder by means of the reading unit before or during the insertion of the holder. If the labels are read during the insertion of the holder, each inserted container can be assigned to a certain position in the holder and accordingly in the pivot receptacle or in the mixing apparatus. If reading is to take place during insertion, the holder must be inserted into the pivot receptacle. If the reading is carried out before insertion, it is necessary to ensure that the holder is inserted correctly. To prevent incorrect insertion, the first and second receptacles of the pivot receptacle and, accordingly, the first and second ends of the holder may be differently shaped.

In an embodiment, the method comprises the steps:
Removal of fluids from the containers in the mixing apparatus after pivoting the pivot receptacle;
Feeding of fluids into the containers in the mixing apparatus before the pivot receptacle is pivoted.

For example, the contents of a mother tube containing whole blood, for example, can be mixed separately or with additional substances. After mixing, part of the whole blood can be re-pipetted from the mother tube to a daughter tube. The daughter tube may be empty beforehand or may contain a substance such as a reagent. Afterwards, the contents of the daughter tube can be mixed again. After mixing, the holder and its containers can be removed from the mixing apparatus and fed to an analyzer.

The mentioned embodiments of the method can be used in any combination, as long as they do not contradict each other.

BRIEF DESCRIPTION OF THE FIGURES

Exemplary embodiments of the present invention are explained in more detail below by reference to the drawings. These are for explanatory purposes only and are not to be interpreted in a restrictive manner, wherein.

DETAILED DESCRIPTION OF THE INVENTION

Figure 1:
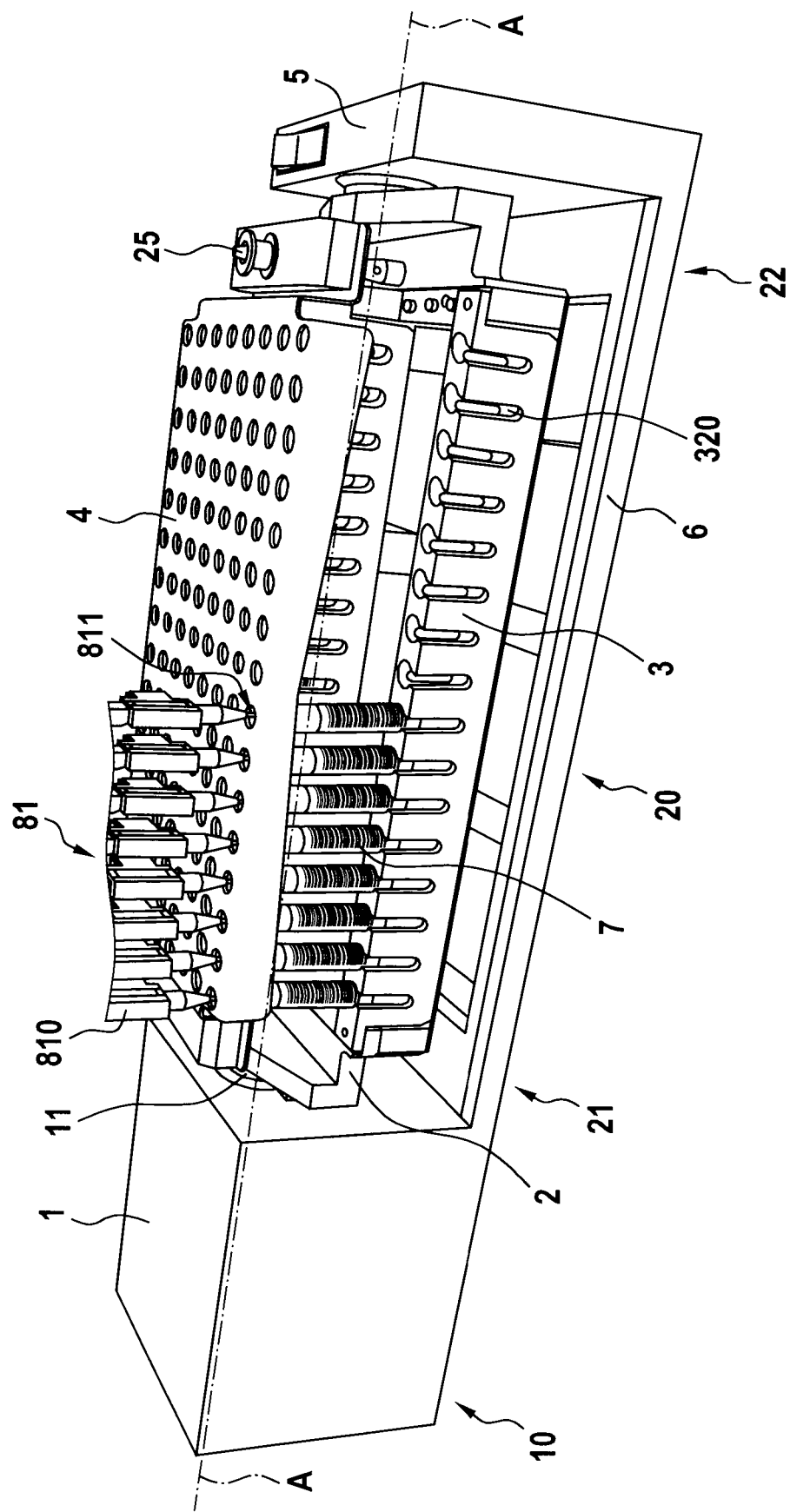
FIG. 1 shows a perspective view of a first embodiment of a mixing apparatus according to the invention.

FIG. 1 shows a perspective view of a first embodiment of a mixing apparatus according to the invention. The mixing apparatus comprises a drive unit 1, having a drive 10, which is operatively connected to a rotatable shaft 11 and which can pivot or rotate it about a pivot axis A. The pivot axis A is essentially horizontally aligned. A pivot receptacle 2 is operatively connected to shaft 11 and thus pivotable about the pivot axis A by drive 10. The pivot receptacle comprises a base plate 20, which comprises first receptacles 21 in an area near the shaft and second receptacles 22 in an area remote from the shaft. A holder 3 can be removably arranged in each case in a first receptacle 21 and a second receptacle 22 aligned with said first receptacle in the direction of the pivot axis.

Containers 7 can be accommodated in holder 3. The holder has lateral slots 320, through which labels on the containers 7 are visible. The mixing apparatus comprises a bearing unit 5, which is arranged on the side of the pivot receptacle 2, which is opposite the drive unit 1. The pivot receptacle 2 is mounted in bearing unit 5 so that it can pivot about the pivot axis A. Bearing unit 5 is connected and aligned with drive unit 1 via a connecting plate 6. A retaining element 4 is removably arranged in third receptacles 25 above the holders 3 and the containers 7 accommodated therein. The distance between retaining element 4 and the holders 3 is dimensioned such that the surface of the retaining element 4 directed against the holders 3 rests essentially against the free ends of the containers 7 received in the holder 3 or has a distance of a few millimeters, for example 1 to 5 millimeters. Also shown is a pipetting unit 81 with a transport unit 810 and pipette tips 811, wherein the transport unit 810 has aligned the pipette tips 811 with the containers 7 and has lowered the pipette tips 811 so that they protrude into the inside of the containers 7.

Figure 2:
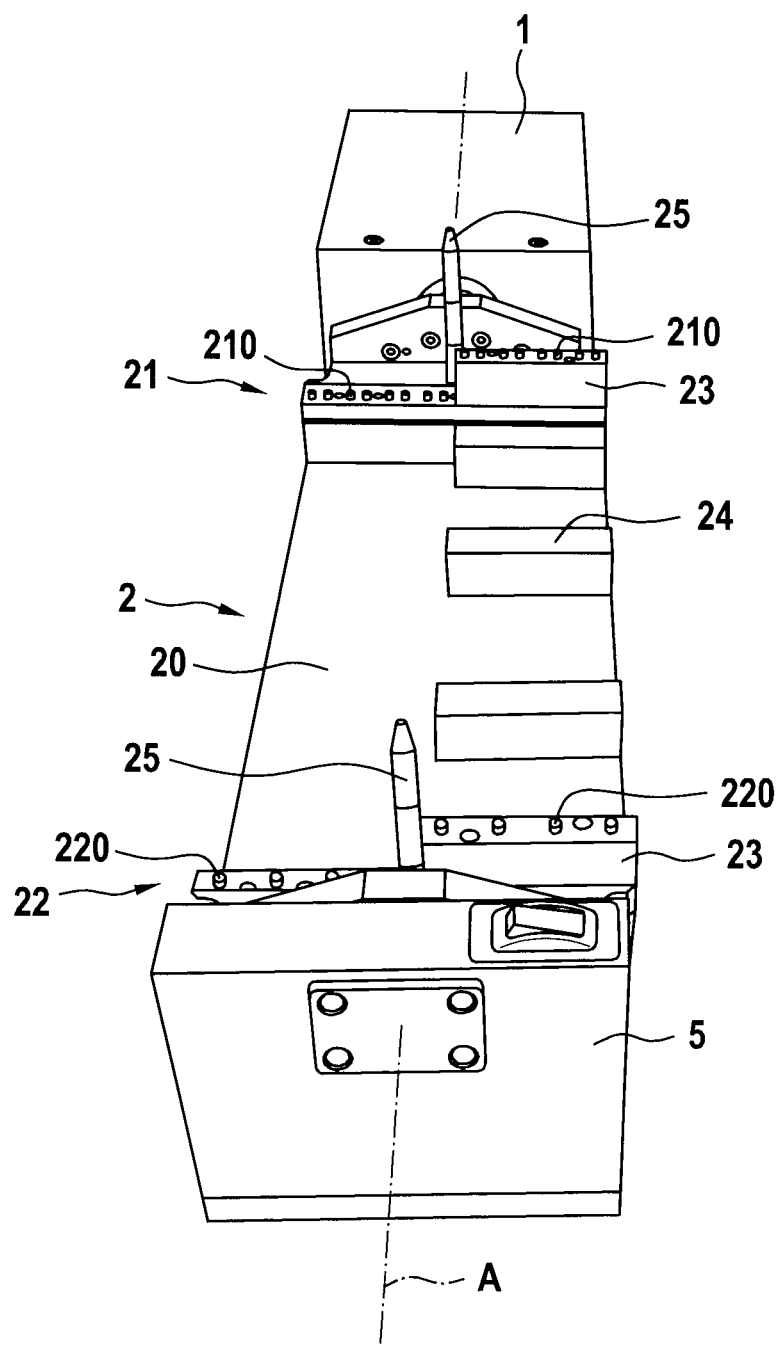
FIG. 2 shows the mixing apparatus of FIG. 1, without inserted holders and without retaining element.

FIG. 2 shows the mixing apparatus of FIG. 1, without inserted holders and without retaining element. In the embodiment shown, the first receptacles 21 and the second receptacles 22 comprise a low region and a raised region, wherein the low region has a smaller distance from the base plate 20 and the raised region has a larger distance from the base plate 20. Instead of the raised areas, first spacers 23 can be provided, which are placed on the low areas and increase the distance from the base plate 20. The first and second holders 21, 22, as well as the first spacers 23, comprise elevations 210, 220 in the form of cylindrical pins. Second spacers 24 are provided on the base plate 20, which are arranged essentially evenly distributed between the first receptacles 21 and the second receptacles 22 of the raised areas. On the side of the pivot unit 2 facing the drive unit 1 and on the side of the pivot unit 2 facing away from drive unit 1, a respective third receptacle 25 in the form of a cylindrical pin is arranged. In the raised area of the receptacles, i.e. in the area of the receptacles with the first spacers 23, the distance of the holder 3 from base plate 20 is greater by the thickness of the third spacers 23 than in the remaining area.

Figure 3:
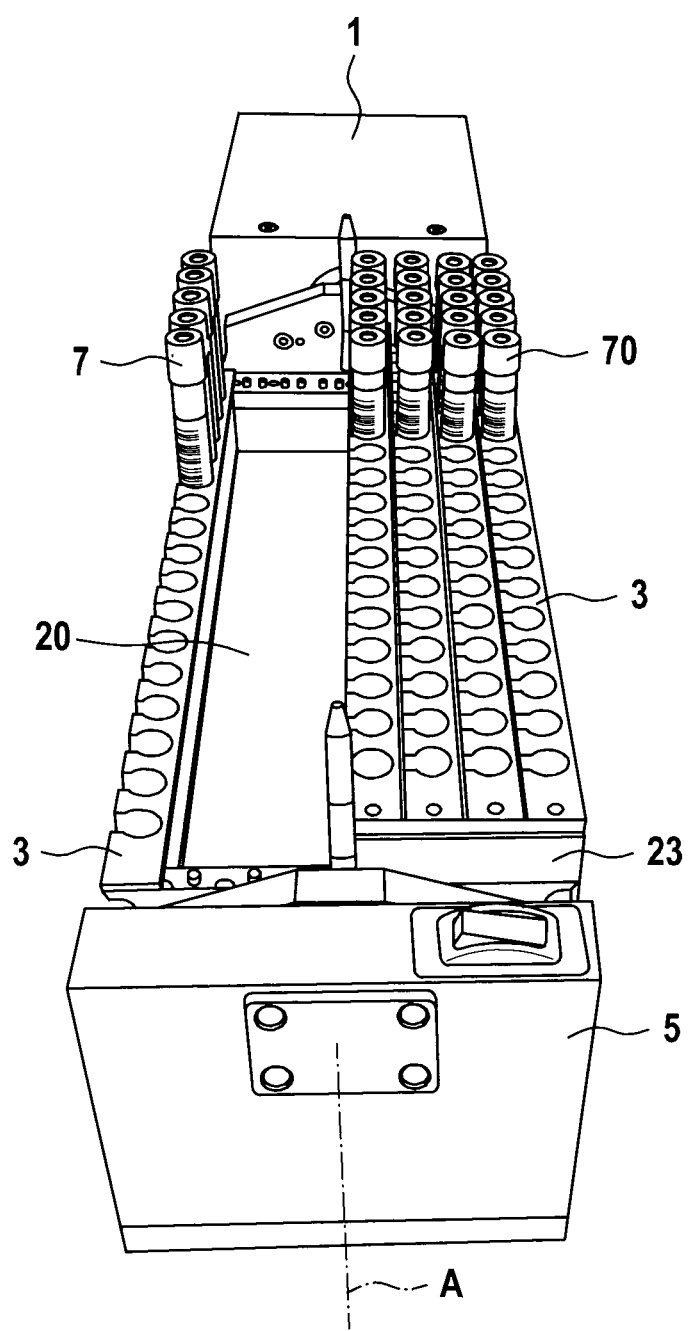
FIG. 3 shows the mixing apparatus of FIG. 2 with inserted holders in which containers are inserted.

FIG. 3 shows the mixing apparatus of FIG. 2 with inserted holders 3, into which containers 7, 70 are inserted. The longer containers 7 are arranged with their holders 3 in the receptacles without first spacers 23 and the shorter containers 70 are arranged with the same holders 3 in the spacers 23. The first spacers 23 are matched with the shorter containers 7 and the longer containers 70 in such a way that the topsides of all containers 7, 70 are aligned with each other.

Figure 4:
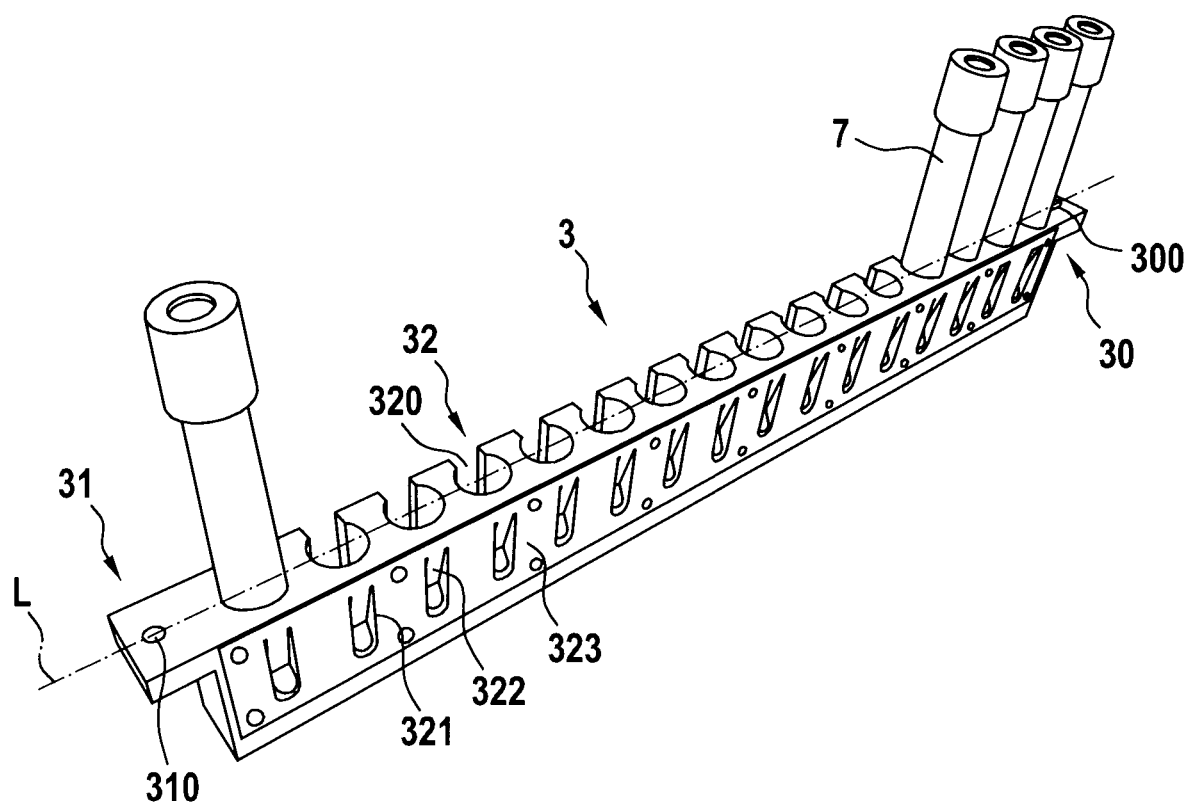
FIG. 4 shows a perspective view of a holder for containers that can be inserted into the mixing apparatus according to the invention.

FIG. 4 shows a perspective view of a holder 3 for container 7, which can be inserted into the mixing apparatus according to the invention. The holder 3 extends essentially along a longitudinal axis L and comprises a first end 30 and an opposite second end 31, with which each holder 3 can be inserted into the first and second receptacles 21, 22 of the pivot receptacle 2. The two ends 30, 31 are designed as tabs which extend laterally outwards along the longitudinal axis L from the upper surface of the holder 3. The two ends 30, 31 each include a recess 300, 310 in the form of a through hole with a circular cross-section. The cross-section of the bores 300, 310 is matched to the cross-section of the complementary pins 210,220 in such a way that the holders 3 can be inserted into or removed from the pivot receptacle 2 with little effort. Along the longitudinal axis L, container receptacles 32 are formed in the holder 3 in the form of cylindrical bores which extend from the upper side of the holder downwards over part of the height of the holder 3. Each container receptacle 32 comprises a slot 320 and a window 321, both extending laterally outwards from the container receptacle 32 transverse to the longitudinal axis L, wherein the window 321 is arranged on the side of the container receptacle 32 opposite the slot. On the side of the holder 3, which comprises the windows 321, there is a tab plate 323, which comprises clamping tabs 322, each of which projects through a window 321 into the interior of the container receptacle. With the clamping tabs 322, the containers 7 accommodated in holder 3 can be clamped laterally in the container receptacles 32 so that they cannot fall out of the holder when it is turned upside down.

Figure 5:
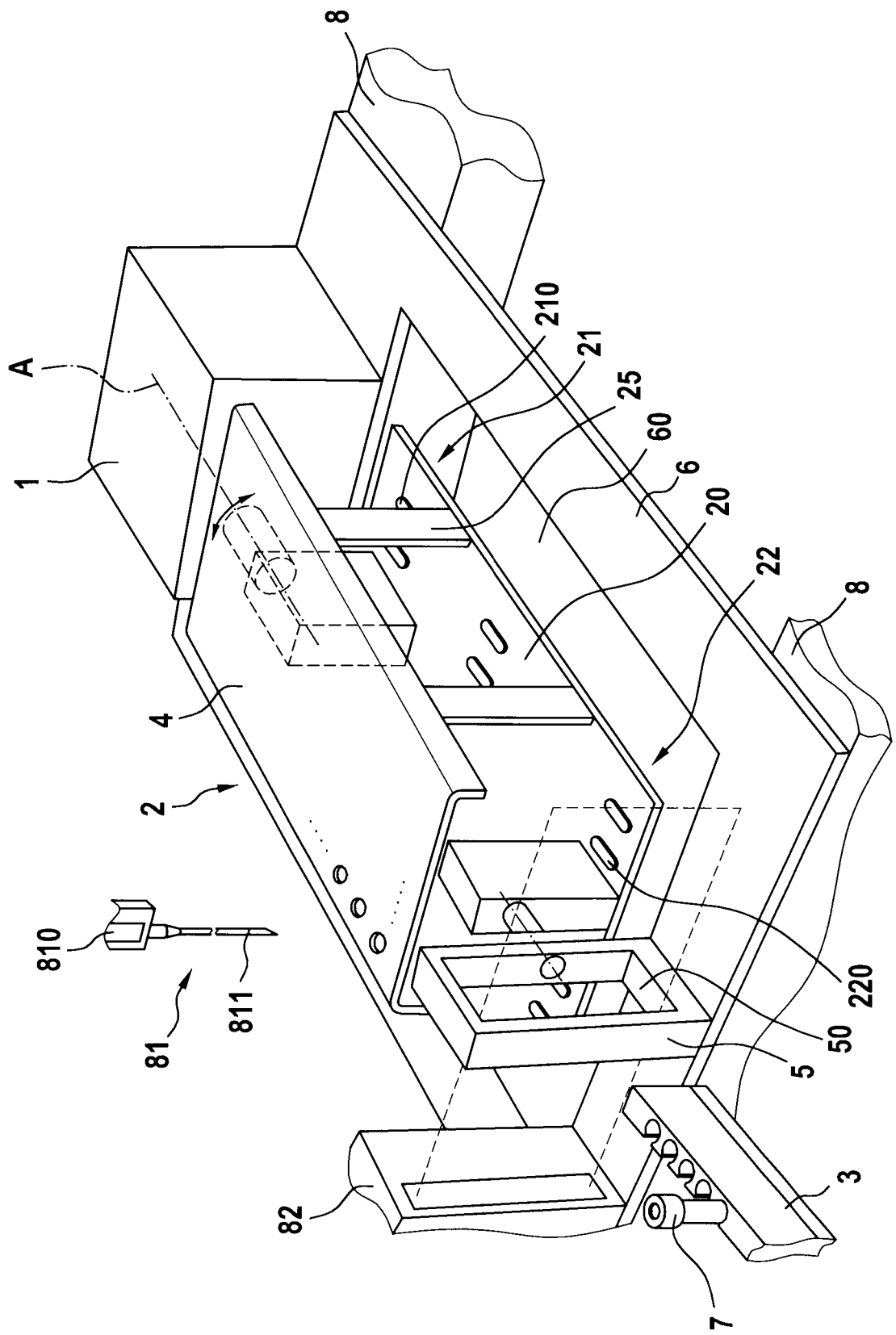
FIG. 5 shows an outlined perspective view of a second embodiment of a mixing apparatus according to the invention.

FIG. 5 shows an outlined perspective representation of a second embodiment of a mixing apparatus according to the invention. In this embodiment, the connecting plate 6 comprises a recess 60 between the drive unit 1 and the bearing unit 5. The pivot receptacle 2 is arranged and mounted between the drive unit 1 and the bearing unit 5 such that the surface of the base plate 20 is aligned substantially flush with the surface of the connecting plate 6. The pivot receptacle 2 is freely pivotable in the recess 60 in the connecting plate 6 with the drive unit 1. The connecting plate is arranged directly on a machine stand 8. The elevations 210, 220 of the first and second receptacles 21, 22 of the pivot receptacle 2 are designed as sliding blocks which extend away from the base plate 20. The sliding blocks are aligned with respect to the pivot axis A and are arranged side by side in rows transversely to the pivot axis A. On the base plate 20, third receptacles 25 are arranged, with which the retaining element 4 is permanently connected to the base plate 20. The retaining element 4, in turn, has holes. In this illustration, a reading unit 82 is located on the connection plate 6, on the side of bearing unit 5, and the bearing unit comprises a recess 50, which allows the reading unit 82 to recognize and read labels on both sides of bearing unit 5. With such an arrangement, the containers 7 can be inserted at any position in the holder 3. However, care must be taken that the labels on the containers 7 are aligned in such a way that they can be read by the reading unit 82 when inserting or pushing in the holder 3 into the pivot receptacle 2. Thus, each container can be identified and at the same time the position of each container 7 in holder 3 can be determined. A pipetting unit 81 with a transport unit 810 and with pipette tips 811 is also shown in part, wherein the pipette tips 811 are movable in space at least above the mixing apparatus by means of the transport unit 810. This arrangement allows the addition or removal of fluids from the containers 7 accommodated in the mixing apparatus, so that fluids can also be re-pipetted in the mixing apparatus before or after mixing.

Figure 6:
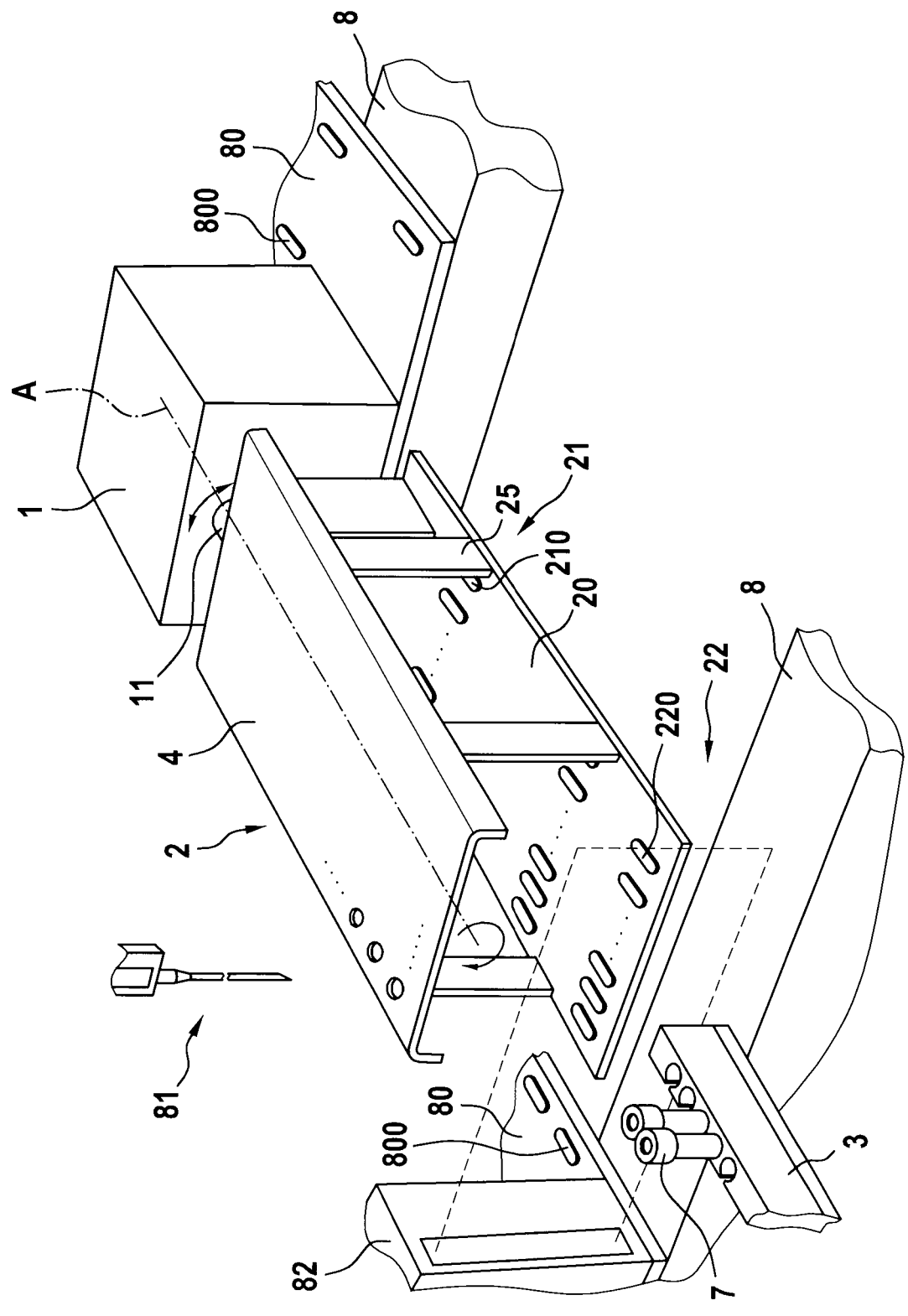
FIG. 6 shows an outlined perspective view of a third embodiment of a mixing apparatus according to the invention.

FIG. 6 shows an outlined perspective representation of a third embodiment of a mixing apparatus according to the invention. Unlike the mixing apparatus in FIG. 5, this embodiment does not include a bearing unit 5 and therefore does not require a connection plate 6. The drive unit 1 and the reading unit 82 are arranged on a working surface 80, which is arranged on the machine stand 8. Receiving elements 800 are provided on the work surface 80, which in this embodiment are identical to the elevations 210, 220 and with which the drive unit 1 and the reading unit 82 are arranged, aligned and detachably attachable on the work surface 80. The pivot receptacle 2 is only mounted on the side of the shaft 11, i.e. on the side of drive unit 1. The side of the pivot receptacle 2, which faces drive unit 2, is free-floating. With such an arrangement, the holders 3 with the containers 7 accommodated therein can be pushed into them unhindered and at any position of the pivot receptacle 2. The container 7 and its position in the holder 3 can again be detected during insertion, which considerably increases process reliability.

Figure 7:
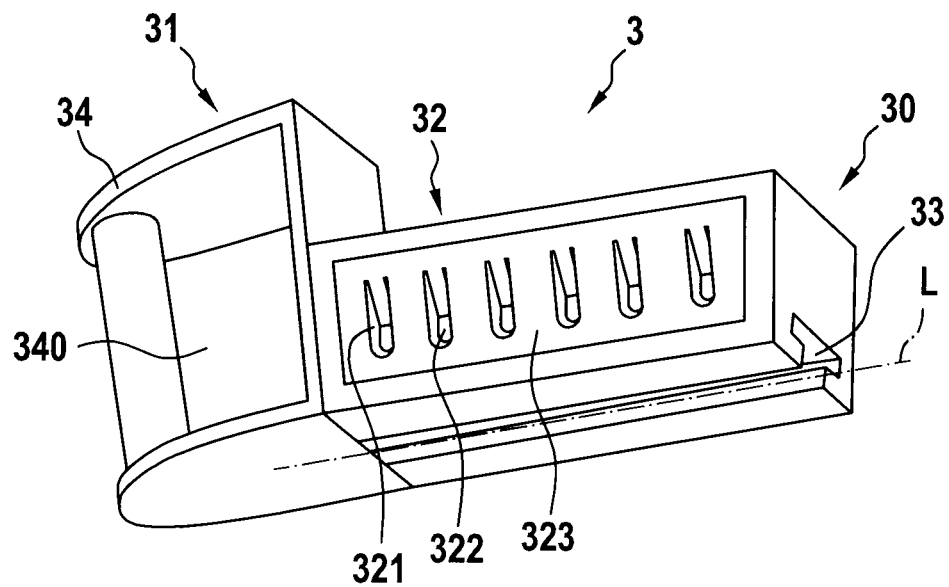
FIG. 7 shows an outlined perspective view of a holder that can be inserted into a mixing apparatus of the second and third embodiment.

FIG. 7 shows an outlined perspective representation of a holder 3 which can be inserted into the mixing apparatus of the second or third embodiment. The holder 3 essentially corresponds to that of FIG. 4, i.e. it extends along the longitudinal axis L, has container receptacles 32 which comprise a slot 320 and a window 321 and has clamping tabs 322 which are integrally designed together with the tab plate 323 and which project through the windows 321 into the interior of the container receptacles 32. In addition, the holder 3 comprises a groove 33, which is arranged on the underside of the holder 3, i.e. on the side of the holder 3 which is opposite the container receptacles 32. Shown is a T-slot. Alternatively, a dovetail groove or another retaining groove can be provided. The groove 33 extends along the longitudinal axis L, at least over the area of the holder 3, which comprises the container receptacles 32. The groove 33 is open at the first end 30 of the holder 3, so that the elevations 210, 220 can easily be retracted into the groove 33. On the second side 31 of holder 3, a handle 34 is arranged, with which holder 3 can easily be gripped by hand. A recess 340 is provided in handle 34, which enables the reading unit 82 to recognize that the holder 3 is completely inserted into the pivot receptacle 2.

Figure 8:
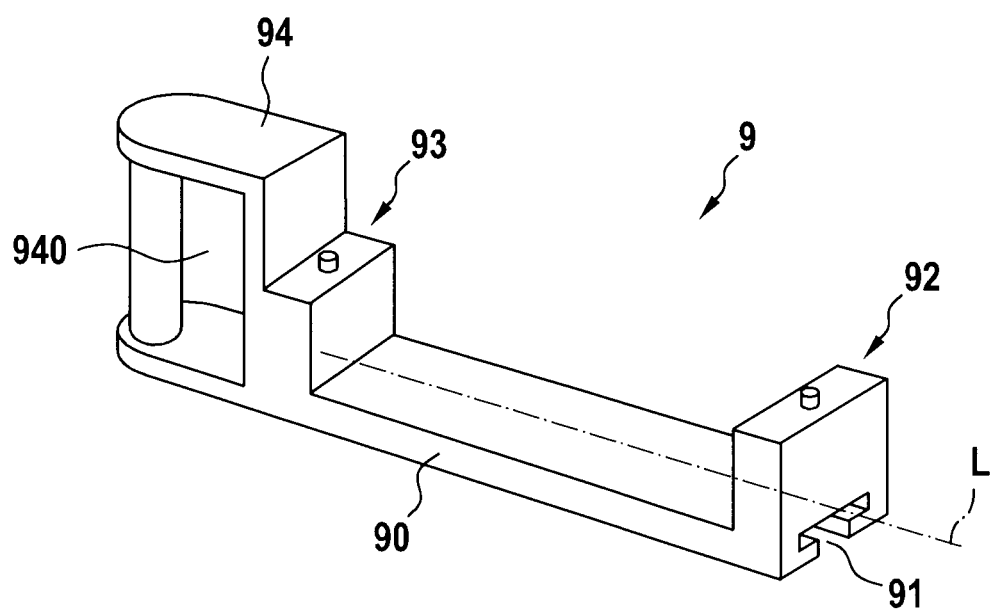
FIG. 8 shows an outlined perspective view of a handling unit that can be inserted into a mixing apparatus of the second and third embodiment.

FIG. 8 shows an outlined perspective representation of a handling unit 9 which can be inserted into the mixing apparatus of the second or third embodiment. The handling unit 9 is designed in such a way that it can accommodate a holder 3 according to FIG. 4. Accordingly, first and second receptacles 92, 93 are provided, which are arranged complementary to the first and second ends 30, 31 of holder 3. The receptacles 92, 93 of the handling unit 9 are connected by a plate 90, which extends along the longitudinal axis L. A groove 91 is provided on the underside of the plate 90, i.e. on the side of the plate that is opposite the receptacles 92, 93. The groove 91 is designed as a T-slot or the like and extends at least over the area of plate 90, which lies between the two receptacles 92, 93. On the side of the first receptacle 92 the groove 91 is formed open towards the outside. A handle 94 with a recess 940 is provided on the side of the second receptacle 93. Spacers can be inserted into handling unit 9, similar to the spacers described in FIG. 2. Alternatively, handling units 9 with differently designed plates 90 or receptacles 92, 93 can be provided.

Figure 9:
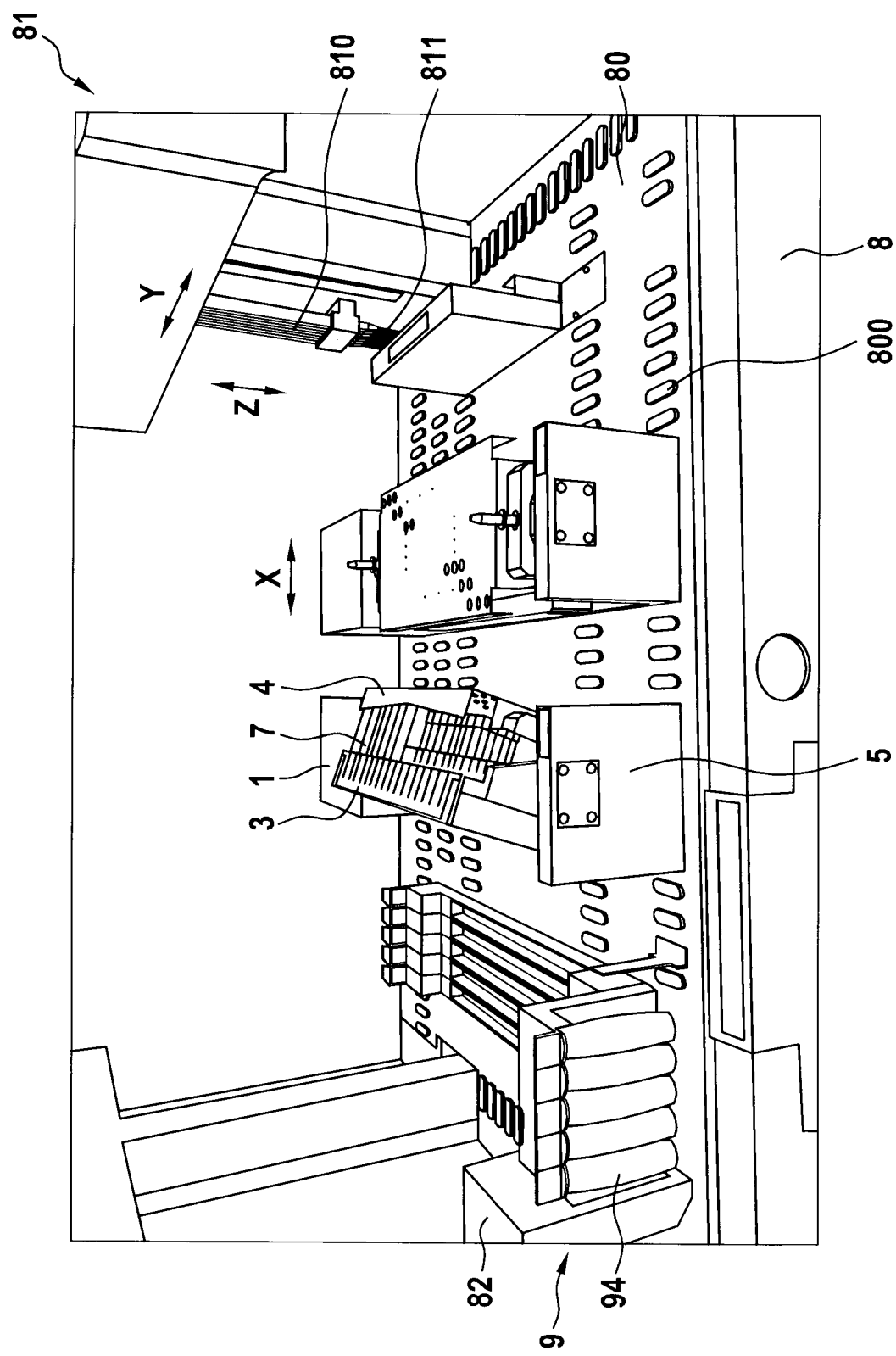
FIG. 9 shows a perspective view of a mixing plant with a mixing apparatus of FIG. 1.

FIG. 9 shows a perspective view of a mixing plant with a mixing apparatus of FIG. 1, which is oriented in a tilted manner, and a non-tilted mixing apparatus. Both devices are arranged on the work surface 80 with receiving elements 800, which are arranged on the machine stand 8. The mixing plant further comprises the pipetting unit 81 with the transport unit 810 and the pipette tips 811. The transport unit 810 can move the pipette tips 811 in a first horizontal direction X, a second horizontal direction Y and a vertical direction Z over the work surface 80. A reading unit 82 is located next to the mixing apparatuses on the work surface 80. The reading unit 82 is also aligned and fixed to the work surface 80 with the receiving elements 800. In front of the reading unit 82, handling units 9 with handles 94 can be pushed over the receiving elements 800 to recognize the labels on the containers 7 arranged in holder 3.

LIST OF REFERENCE NUMERALS

| | | | |
|---|---|---|---|
| 1 | Drive unit | 33 | Groove |
| 10 | Drive | 34 | Handle |
| 11 | Shaft | 340 | Recess |
| 2 | Pivot receptacle | 4 | Retaining element |
| 20 | Base plate | 5 | Bearing unit |
| 21 | First receptacle | 50 | Recess |
| 210 | Elevation | 6 | Connecting plate |
| 22 | Second receptacle | 60 | Recess |
| 220 | Elevation | 7 | Container |
| 23 | First spacers | 70 | Container |
| 24 | Second spacers | 8 | Machine stand |
| 25 | Third receptacle | 80 | Working surface |
| 3 | Holder | 800 | Receiving elements |
| 30 | First end | 81 | Pipetting unit |
| 300 | Recess | 810 | Transport unit |
| 31 | Second End | 811 | Pipette tip |
| 310 | Recess | 82 | Reading unit |
| 32 | Container receptacle | 9 | Handling unit |
| 320 | Slot | 90 | Plate |
| 32 | Window | 91 | Groove |

-continued

| 322 | Clamping tab | 92 | First receptacle |
| --- | --- | --- | --- |
| 323 | Tab plate | 93 | Second receptacle |
| 94 | Handle | A | Pivot axis |
| 940 | Recess | L | Longitudinal axis |

The invention claimed is:

1. A mixing apparatus, comprising:
a drive unit (1) having a drive (10) and a shaft (11) which is pivotable about a pivot axis (A) and is operatively connected to the drive (10),
a pivot receptacle (2) which is arranged on the shaft (11),
at least one holder (3) for standing reagent tubes or perforable ampoules (7), and
a retaining element (4),
wherein the pivot axis (A) is aligned substantially horizontally,
wherein the pivot receptacle (2) comprises a base (20) on which first and second receptacles (21, 22) are provided, which extend away from the base (20) and into which the at least one holder (3) for standing reagent tubes or perforable ampules (7) is inserted, and on which third receptacles (25) are provided on the side of the first and second receptacles (21, 22), with which the retaining element (4) is arranged at least in the region between the first and second receptacles (21, 22) spaced apart from the base (20) in a fixed or removable manner
wherein each holder (3) comprises a plurality of container receptacles (32) arranged along its longitudinal axis (L) and formed between its two ends (30, 31),
characterized in that the retaining element (4) comprises a perforated plate having holes, wherein the holes are arranged so that they are aligned with the container receptacles (32) formed in the holder (3), and in that the internal dimensions of the holes are smaller than the internal dimensions of the container receptacles (32).

2. The mixing apparatus according to claim 1, wherein the pivot receptacle (2) can be pivoted by any angle in both directions about the pivot axis (A).

3. The mixing apparatus according to claim 1, comprising a control unit, with which the pivot angle, the pivot speed and the pivot direction can be adjusted.

4. The mixing apparatus according to claim 1, wherein the first receptacles (21) are arranged in a shaft-near region of the base (20), and wherein the second receptacles (22) are arranged in a shaft-remote region of the base (20), and wherein each holder (3) is inserted with its first end (30) into the first receptacle (21) and wherein each holder (3) is inserted with its second end (31) into the second receptacle (22).

5. The mixing apparatus according to claim 1, wherein the first and second receptacles (21, 22) comprise elevations (210, 220) which may protrude into correspondingly complementary recesses (300, 310) of the ends (30, 31) of the holders (3).

6. The mixing apparatus according claim 1, wherein a plurality of first and second receptacles (21, 22) are arranged side by side in a direction transverse to the pivot axis (A).

7. The mixing apparatus according to claim 1, comprising first spacers (23) that are inserted into the first and second receptacles (21, 22) and into which each holder (3) for the containers (7) is inserted, and second spacers (24) which are arranged between the first and second receptacles (21, 22) and on which each holder (3) for the containers (7) is resting.

8. The mixing apparatus according to claim 1, wherein the third receptacles (25) are designed such that the retaining element (4) can be arranged in a removable or displaceable manner therein.

9. The mixing apparatus according to claim 1, comprising a bearing unit (5) which is opposite the drive unit (1) with respect to the pivot receptacle (2) and in which the pivot receptacle (2) is pivotably mounted in alignment with the shaft (11).

10. A mixing plant, comprising:
a machine stand (8) on which a mixing apparatus in accordance with claim 1 is arranged.

11. The mixing plant according to claim 10, comprising a pipetting unit (81) with which fluids can be supplied to or removed from standing reagent tubes or perforable ampoules (7) located in the mixing apparatus.

12. The mixing plant according to claim 11, wherein the pipetting unit (81) comprises a transport unit (810) on which pipette tips (811) are arranged and with which the pipette tips (811) are movable horizontally and/or vertically in a region above the machine stand (8) or above the working surface (80).

13. The mixing plant according to claim 11, comprising a reading unit (82), with which labels are readable from the standing reagent tubes or perforable ampoules (7) to be received by the mixing apparatus.

14. A method for operating a mixing apparatus or a mixing plant, comprising the steps of:
providing a mixing apparatus in accordance with claim 1;
inserting a holder (3) with standing reagent tubes or perforable ampoules (7) arranged therein into the receptacles (21, 22) of the pivot receptacle (2); and
pivoting the pivot receptacle (2) about the pivot axis (A) with the drive unit (1).

15. The method according to claim 14, comprising the steps of:
removing the retaining element (4) before inserting the holder (3); and
attaching the retaining element (4) after inserting the holder (3).

16. The method according to claim 14, comprising the step of:
reading labels from the standing reagent tubes or perforable ampoules (7) arranged in a holder (3) by means of the reading unit (82) before or during the insertion of the holder (3).

17. The method according to one of claim 14, comprising at least one of the steps:
removing fluids from the standing reagent tubes or perforable ampoules (7) disposed in the mixing apparatus after pivoting the pivot receptacle (2);
feeding of fluids into the standing reagent tubes or perforable ampoules (7) disposed in the mixing apparatus before pivoting the pivot receptacle (2).

* * * * *